US006994761B2

(12) United States Patent
Klemp et al.

(10) Patent No.: US 6,994,761 B2
(45) Date of Patent: Feb. 7, 2006

(54) DISPOSABLE ABSORBENT GARMENT SUCH AS A DIAPER OR TRAINING PANTS AND A PROCESS OF MAKING THE SAME

(75) Inventors: Walter V. Klemp, Abilene, TX (US); Daniel D. Gardner, Jr., Petosky, TX (US)

(73) Assignee: Fameccanica Data S.p.A., Sambuceto di San Giovanni Teatino (IT)

( * ) Notice: Subject to any disclaimer, the term of this patent is extended or adjusted under 35 U.S.C. 154(b) by 471 days.

(21) Appl. No.: 10/358,043

(22) Filed: Feb. 4, 2003

(65) Prior Publication Data

US 2003/0135187 A1 Jul. 17, 2003

Related U.S. Application Data

(62) Division of application No. 09/580,282, filed on May 30, 2000, now Pat. No. 6,572,595.

(51) Int. Cl.
*B32B 31/00* (2006.01)

(52) U.S. Cl. .................... 156/73.3; 156/73.1; 156/163; 156/229; 156/251; 156/252; 156/290; 156/308.4

(58) Field of Classification Search ............... 156/73.1, 156/73.3, 160, 163, 164, 229, 251, 252, 253, 156/268, 290, 308.2, 308.4, 580.1, 280.2; 264/442, 443, 444, 445
See application file for complete search history.

(56) References Cited

U.S. PATENT DOCUMENTS

| 3,860,003 A | 1/1975 | Buell |
| 4,695,278 A | 9/1987 | Lawson |
| 4,743,246 A | 5/1988 | Lawson |

(Continued)

FOREIGN PATENT DOCUMENTS

WO WO 9605792 2/1996

*Primary Examiner*—James Sells
(74) *Attorney, Agent, or Firm*—Alberto Q. Amatong, Jr.; The Morris Law Firm, PC

(57) ABSTRACT

A disposable absorbent garment includes a topsheet, a backsheet, and an absorbent core disposed between the topsheet and the backsheet. The topsheet, the backsheet, and the absorbent core form a layered assembly including a front region, a back region, and a crotch region disposed between the front region and the back region. The garment is characterized by a vertical longitudinal plane that extends substantially centrally through the front, back and crotch regions. Each of the front and back regions includes a pair of ear portions extending in substantially opposite lateral directions with respect to the longitudinal plane. Each ear portion is a breathable stretchable layer assembly having a plurality of vent sites. Further, each ear portion includes an outer layer that is an extension of the backsheet and which extends laterally to the side edge of the ear portion, and an inner layer that is an extension of the topsheet and which also extends laterally to the side edge of the ear portion. The ear portion also includes a stretchable material layer secured between the inner layer and the outer layer. The topsheet includes a central section that is generally disposed in a center section of the garment and over the core. Each of a pair of side sections of the topsheet extends laterally and forms the inner layer of two of the ear portions. The side section also forms an outer wall section of a leg cuff that extends longitudinally along the lateral side of the core. An inner wall section of the leg cuff is a portion of a substantially impervious material that extends below the leg cuff to sealingly engage the side edge of a polymeric film barrier disposed underneath the core. The substantially impervious material and the polymeric film barrier combine to form a substantially impervious containment structure about the sides and bottom of the core.

19 Claims, 4 Drawing Sheets

U.S. PATENT DOCUMENTS

| | | |
|---|---|---|
| 4,747,895 A * | 5/1988 | Wallerstein et al. ....... 156/73.3 |
| 4,770,656 A | 9/1988 | Proxmire et al. |
| 4,842,596 A | 6/1989 | Kielpikowski et al. |
| 4,846,825 A | 7/1989 | Enloe et al. |
| 4,847,134 A | 7/1989 | Fahrenkrug et al. |
| 4,857,067 A | 8/1989 | Wood |
| 4,887,602 A | 12/1989 | O'Leary |
| 4,938,753 A | 7/1990 | Van Gompel et al. |
| 5,019,066 A | 5/1991 | Freeland et al. |
| 5,246,433 A | 9/1993 | Hasse et al. |
| 5,254,111 A | 10/1993 | Cancio et al. |
| 5,263,948 A | 11/1993 | Karami et al. |
| 5,292,316 A | 3/1994 | Suzuki |
| 5,569,234 A | 10/1996 | Buell et al. |
| 5,571,096 A | 11/1996 | Dobrin et al. |
| 5,628,737 A | 5/1997 | Dobrin et al. |
| 5,718,698 A | 2/1998 | Dobrin et al. |
| 5,735,984 A * | 4/1998 | Hoff et al. .................. 156/73.3 |
| 5,879,494 A * | 3/1999 | Hoff et al. .................. 156/73.3 |
| 5,911,713 A | 6/1999 | Yamada et al. |
| 6,277,224 B1 * | 8/2001 | Muesch et al. ............. 156/73.3 |
| 6,340,782 B1 * | 1/2002 | Kling et al. ................. 604/366 |

* cited by examiner

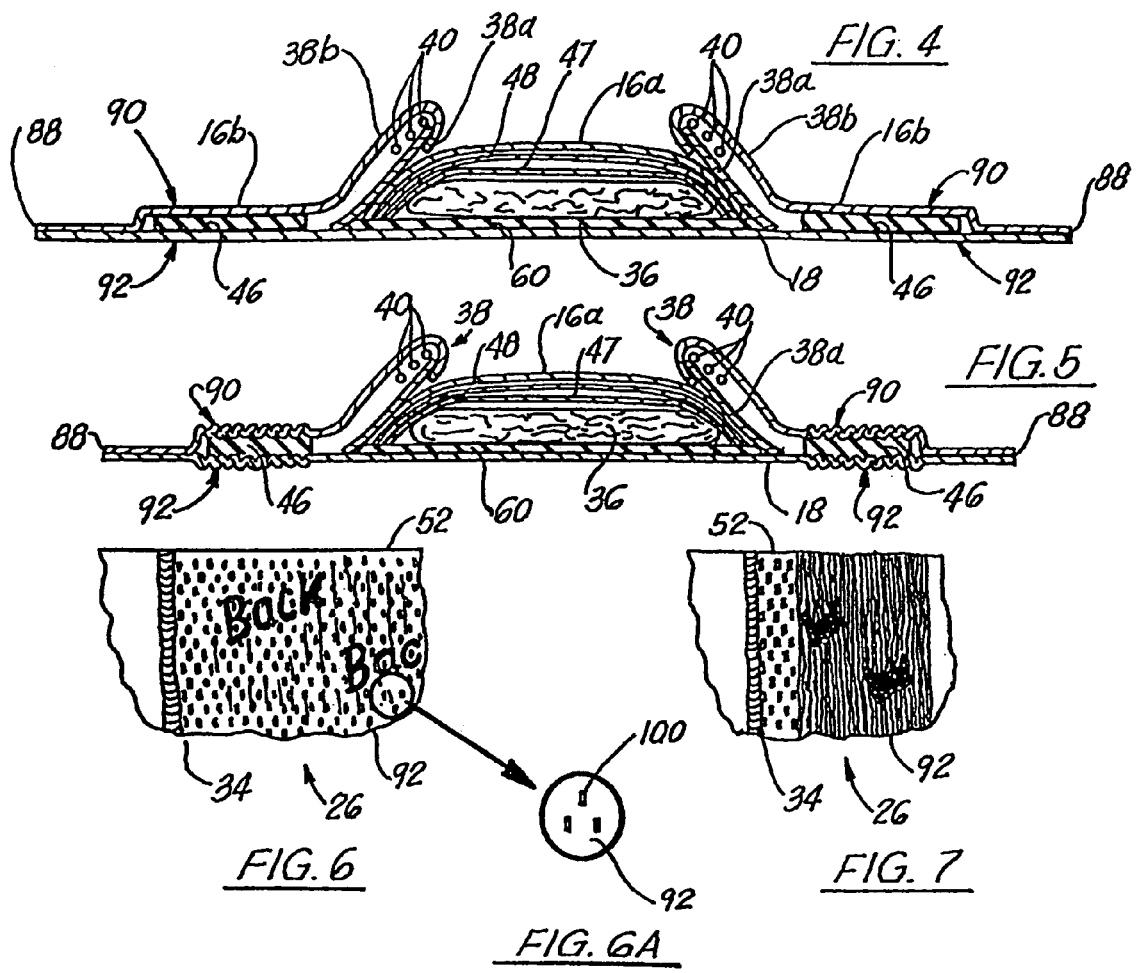

DISPOSABLE ABSORBENT GARMENT SUCH AS A DIAPER OR TRAINING PANTS AND A PROCESS OF MAKING THE SAME

The present application is a continuation application of application Ser. No. 09/580,282 filed on May 30, 2000 U.S. Pat. No. 6,572,595. The above application is hereby incorporated by reference for all purposes and made a part of the present disclosure.

BACKGROUND OF THE INVENTION

Disposable absorbent garments contemplated by the invention include disposable diapers, disposable pull-on garments, and the like. These garments are worn about the lower torso or waist of the user so as to receive and contain urine and other bodily wastes. Disposable diapers are particularly intended for use on infants who depend on a caretaker to fit the diaper. Typically, the infant is laid down while the caretaker places the garment around the waist region of the infant and then secures two ends on each side of the diaper together.

Disposable pull-on garments include training pants, pull-on diapers, disposable underwear, and adult incontinence garments. It is generally expected that the user of any one of these garments will be able to put on and take off the garment on his/her own. As for training pants, these garments are intended for use on a young child just before or about the time the child is ready to graduate from diapers to regular underpants (i.e., during toilet training). Training pants (and other disposable pull-on pants) have closed sides such that the user or care giver raises the garment about the user's legs to put it on and slips the garment downward about the user's legs to take it off. Thus, training pants (and other pull-on pants) are designed to be put on and taken off in the same manner by which regular underpants are put on and taken off. This feature is particularly advantageous in toilet training because it provides an early introduction to underpants and, more specifically, trains the child to wear regular underpants. Similarly, it is advantageous that the training pants fit and look very much like regular underpants so that the child is comfortable in making the transition from training pants to regular underpants.

The principal elements that typically make up the disposable absorbent garments described above are a liquid-permeable inner layer (or topsheet), a liquid-impermeable outer layer (or backsheet) and an absorbent core sandwiched between the inner and outer layers. Elastic members may also be incorporated into different parts of the garments. For example, elastic members may be positioned longitudinally along the diaper, generally outboard of the absorbent core to effect a seal around the buttocks, legs or both of the user. In addition, several elastic members (e.g., in the form of elongated elastic threads) may be positioned laterally throughout the waist region (including the side waist regions) of a disposable absorbent garment to allow the garment to stretch when it is put on and then during wear. In this way, the garment can stretch to accommodate variations in waist size and leg size of the user, while fitting snugly about the waist and legs and without sagging. One drawback, however, is that the elastic strands are visible on the outer surfaces of the garment and can interfere to some extent with decorative or instructional printing displayed on the outer surfaces of the garment.

Despite the increasing acceptance of disposable garments over the traditional cloth diapers, environmental concerns remain. A closely related issue is "source reduction" as it relates to conservation of resources. Accordingly, products which require fewer materials to accomplish the same functionality are particularly desirable.

Moreover, due to the high frequency of use and inherent "disposability" of disposable garments, consumers are very sensitive to the price they pay for the garments. Therefore, it is desirable for manufacturers to provide a more cost-effective disposable absorbent garment.

It is also known to provide disposable garments with separate side waist regions in the form of elastic side panels such as those disclosed in U.S. Pat. No. 4,938,753. The elastic side panels described therein have side edges, which are attached to the outer edges of a central absorbent core assembly. The elastic side panels may be made from various elastomeric materials or combinations thereof and provide a more uniform fit generally more snug than side waist regions having elongated elastic strands. Moreover, the elastic side panels provide outer surfaces, which are more uniform than the outer surfaces on side waist regions having elongated elastic strands. However, the elastomeric material for the side panel does not typically provide for a smooth, even outer surface when the side panels are in either the relaxed state or the stretched state. Accordingly, the side panels are not particularly conducive to having decorative or instructional printing displayed thereon. In addition, the cost of producing separate side panel products is high due to the nature of the materials and the process difficulties of handing multiple web components. Again, the cost is critical to users of disposable garments due to their high rate of use. Furthermore, the separate side panel construction inherently relies on additional seams which detract from the product's appearance, making the product look less like real underwear.

Alternatively, it is known to provide a unitary pair of training pants with elasticized ear flaps such as those disclosed in U.S. Pat. No. 5,246,433. The elasticized ear flaps are formed by sandwiching a relaxed elastomeric element between two material layers of the ear flaps, and adhesively attaching the material layers to the relaxed elastomeric element to form an elastic laminate. The design also calls for mechanically stretching the elastic laminate such that the material layers permanently deform. Although the side waist region according to this design generally provides a more uniform fit than a side waist region having elongated elastic strands, the outside surfaces of the side waist region are not conducive to having decorative or instructional print displayed thereon because the mechanically stretched material layers are uneven and cannot fully return to their original undistorted configuration. Other drawbacks of this and related designs include: 1) poor appearance due to deformation of materials, 2) limited range of stretch, and 3) loss of integrity of the inner and outer layers, weakening the product and forcing the use of higher strength and higher cost elastomers.

SUMMARY OF THE INVENTION

It is, therefore, one object of the invention to provide an improved disposable absorbent garment such as a diaper or adult incontinence garment, and an improved method of making such a garment and/or components of the garment.

In accordance with one aspect of the present invention, a disposable absorbent garment is provided having a topsheet, a backsheet, and an absorbent core disposed between the topsheet and the backsheet. The topsheet, backsheet, and core together form a front region, a back region, and a crotch region disposed between the front region and the back region. To facilitate reference, the garment may be described as having a vertical longitudinal plane that extends substantially centrally through the front, back and crotch regions.

Preferably each of the front and back regions includes a pair of ear portions which, extend in substantially opposite lateral directions with respect to the longitudinal plane. Each ear portion is a breathable, stretchable layer assembly. Preferably, this stretchable layer assembly includes a plurality of breathing or vent sites which are spaced from one another to present a staggered pattern of vent sites on the ear portions. At the vent sites, an outer material layer of the ear portion (e.g., an extension of the backsheet) is bonded with an inner material layer of the ear portion (e.g., an extension of the topsheet). As a result of a bonding process, such as ultrasonic bonding, vent sites are created which include a hole(s) or aperture(s) through the stretchable material layer (and through the inner material layer and the outer material layer) and through which air is passable. The present invention is also directed to a method of making an ear region, side waist region or side panel having such breathable attributes and, alternatively, a method for making a composite web structure or garment having such breathable attributes.

In accordance with another aspect of the invention, a disposable absorbent garment is provided having a topsheet, a backsheet, and an absorbent core disposed between the topsheet and the backsheet. The topsheet, backsheet, and absorbent core form a front region, a back region, and a crotch region disposed between the front region and back regions. Further, each of the front and back regions includes a pair of ear portions extending in substantially opposite lateral directions. Each ear portion has a stretchable layer assembly of an outer material layer, an inner material layer, and a stretchable member or material layer secured therebetween. The outer material layer is an extension of the backsheet and extends laterally to form, at least partially, a side edge of the ear portion (i.e., side edge of the garment). Similarly, the inner material layer is an extension of the topsheet and extends laterally to also form, at least partially, a side edge of the ear portion. Accordingly, an ear portion may be formed that is seamless (i.e., along the outer and inner surfaces) as well as stretchable.

Preferably, the topsheet is a three-piece topsheet assembly consisting of a central section (including a portion generally disposed over the core) and a pair of side or outer sections which form or provide the inner material layers of two of the ear portions (e.g., for the two ear portions or the two right ear portions). Moreover, the garment may include a longitudinally-extending, preferably elasticized, leg cuff spaced in generally parallel relation from each lateral side of the core. The leg cuff may include an outer material, section or layer that is formed from the topsheet (e.g., topsheet side or outer section) and an inner material, section or layer that is substantially impervious.

Further yet, the stretchable material layer may be one that is extendible between a contracted configuration and an extended configuration and is preferably secured to the outer material layer when the stretchable material layer is disposed in the extended configuration. As a result, the outer material layer is subsequently contractible then extendible with the stretchable material layer (and, more particularly, its outer surface is returnable to a substantially smooth and planar configuration).

The invention, therefore, provides a garment with stretchable ear portions that employ a relatively few number of materials and components than is typical and are less expensive to produce. Such attributes are particularly important in products such as diapers and training pants which are consumed by users at a high rate. As compared to prior art products with side panels, the present invention provides a garment with stretchable ear portions or layers which can be (but not necessarily) seamless and thus, have a more desirable appearance, employ fewer components, and are relatively easy to construct. As a result, these inventive garments may be made so as to be relatively less costly and more comfortable to wear. Further, the inventive garment may be relatively lighter than prior art garments, and thus more comfortable to wear.

In accordance with another aspect of the present invention, a disposable absorbent garment is provided having a topsheet, a backsheet, and an absorbent core disposed between the topsheet and the backsheet. The topsheet, backsheet, and the absorbent core also form a front region, a back region, and a crotch region disposed between the front and back regions. Each of the front and back regions includes a pair of ear portions extending in substantially opposite lateral directions. The garment further includes a longitudinally extending leg cuff spaced, in generally parallel relation, from each lateral side of the core. The leg cuff has a first layer formed from a substantially impervious material (e.g., preferably a hydrophobic material such as a polymeric material) and a second layer formed from the topsheet. It is to be understood that the first and second layers of the leg cuff may also be referred to as cuff sections, cuff material or surface, cuff wall and like structure.

For purposes of the present descriptions of the invention, the term "impervious" means impervious to liquid passage. Also, the term "breathable structure" means a structure that substantially allows air to pass therethrough.

In accordance with yet another aspect of the present invention, a disposable absorbent garment is provided having a topsheet, a backsheet, an absorbent core disposed between the topsheet and backsheet, and a polymeric layer (e.g., sheet or mask or film applied onto the backsheet) disposed adjacent the backsheet and generally beneath the core. These components form a garment having a front region, a back region, and a crotch region disposed between the front region and the back region, and a longitudinal plane that extends substantially centrally through the front, back, and crotch regions. Further, each of the front and back regions includes a pair of ear portions extending in substantially opposite lateral directions with respect to the longitudinal plane. The garment also includes a pair of longitudinally extending leg cuffs, wherein each leg cuff is spaced from a lateral side of the core. Further yet, the garment includes a substantially impervious containment structure or barrier defined by the polymeric layer and a pair of substantially impervious sections (e.g. a polymeric side section), extending from one of the leg cuffs to sealingly engage the polymeric layer. In one embodiment, each leg cuff has an outer barrier layer and an inner barrier layer that is a portion of one of the substantially impervious sidewalls. Moreover, the containment structure forms a continuous and substantially impervious barrier (e.g., against core leakage) around the core (i.e., except above the core wherein the waste is received).

In yet another aspect of the invention, there is provided a method of forming a breathable, stretchable section of a disposable absorbent garment, such as a stretchable side panel or ear region. The method includes steps of selecting a first material for a first material layer (e.g., a topsheet non-woven material) and a second material (e.g. a backsheet nonwoven) for a second material layer, whereby the first and second material layers are bondable by an ultrasonic bonding process, and selecting an elastic material (e.g., an elastomer) for a stretchable material layer. The stretchable material layer is positioned between the first and second material layers to form a layer assembly, then one or more bond sites on the layer assembly are targeted for bonding one or more of the material layers together. The method then includes securing the first, second, and stretchable layers together by ultrasonically bonding the first material layer with the second material layer at the one or more sites. Accordingly, an aperture is formed through the stretchable material and the first material layer and the second material layer bond through the aperture, such that the aperture provides a breathable passage therethrough. In a further variation, the targeting step includes longitudinally and laterally spacing the bond sites so as to create a staggered pattern of breathable bond sites on the stretchable section of the garment. This staggered pattern allows for maximum contracted (minimum relaxed) dimensions thus maximizing the fit range of the product.

A stretchable section is therefore made which provides improved comfort and functionality, among other attributes. The method may be employed to form various sections of the garment including an ear portion or waist portion.

It should again be noted that the invention is adaptable to various types of disposable absorbent garments including, but not limited to, disposable diapers, training pants, adult incontinence garments and other pull-on garments.

These and other objects, features and advantages of the present invention will become apparent to those skilled in the art from the following detailed description and the drawings.

BRIEF DESCRIPTION OF THE DRAWINGS

FIG. 4 is a cross sectional view through line 4—4 in FIG. 2;

FIG. 5 is a cross sectional view of the garment in FIG. 4 shown in a relaxed, non-extended configuration;

FIG. 6 is a bottom plan view of a portion of a side waist region of the garment in FIG. 4;

FIG. 6A is a close-up view of a portion in FIG. 6; and

FIG. 7 is a bottom plan view of a portion of a side waist region in FIG. 4 shown in a contracted configuration.

DETAILED DESCRIPTION OF THE DRAWINGS

Figure 1:
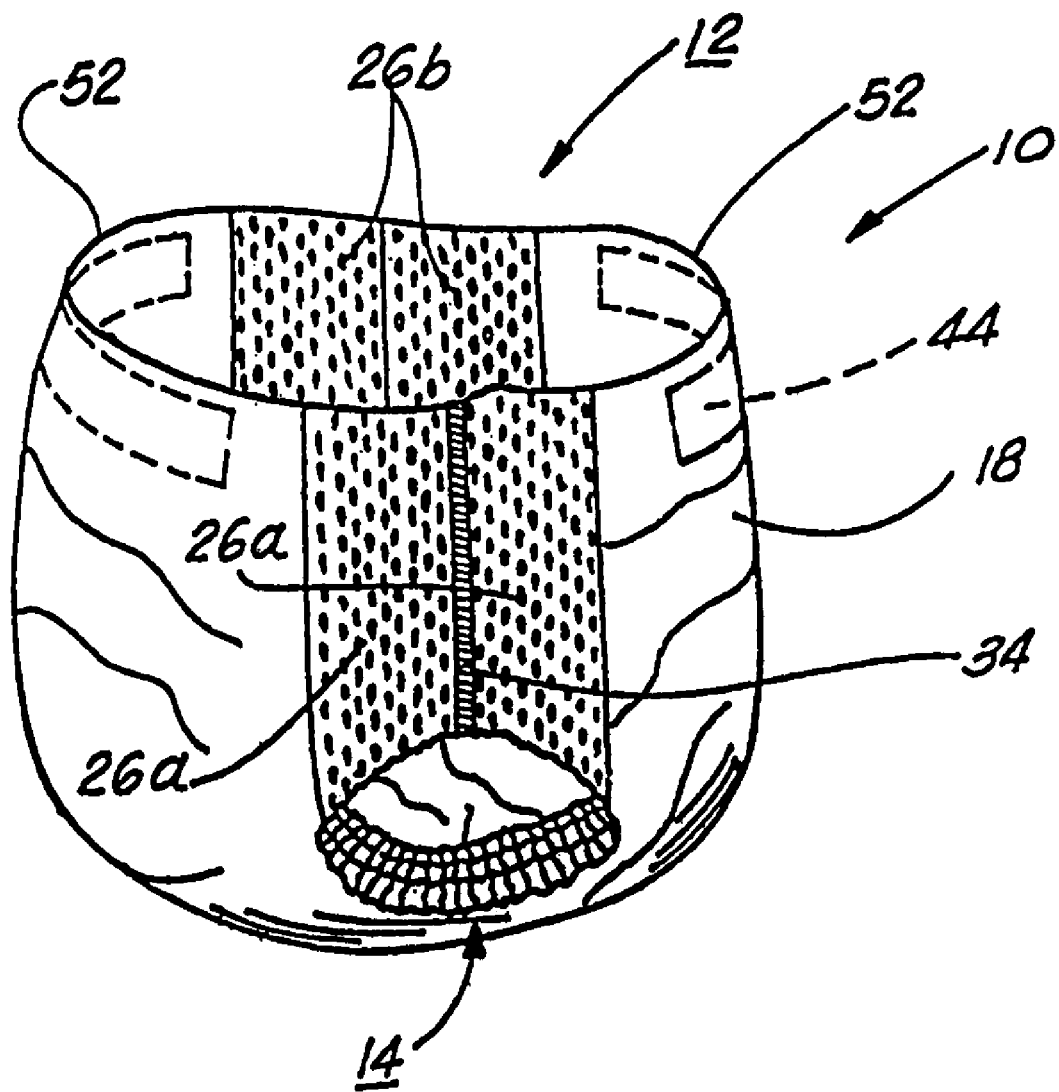
FIG. 1 is a perspective view of a disposable absorbent garment according to one embodiment of the present invention shown as it would appear worn around the waist region of a user.
Figure 2:
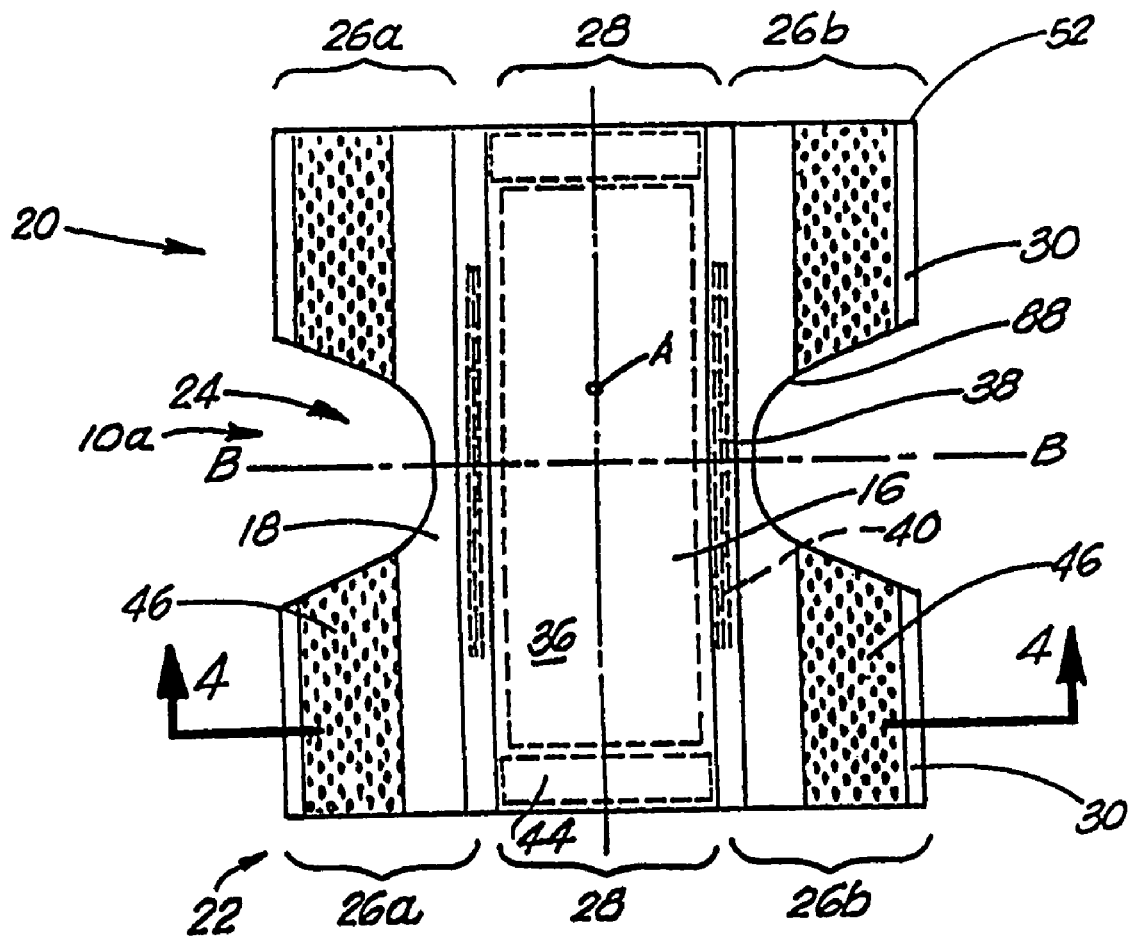
FIG. 2 is a top plan view of a composite web structure of a disposable absorbent garment shown unfolded and extended with portions cut away to reveal an underlying structure.

FIG. 1 depicts a disposable absorbent garment 10 embodying the invention and in the form of a training pant or adult incontinence garment. The garment 10 is formed with a waist opening 12 and two leg openings 14, and is shown, as it would appear worn about the lower torso or waist region of a user. FIG. 2 depicts a composite web structure 10a of the garment 10 in a flat and unfolded configuration, which it assumes during one point in the manufacturing process when it is stretched in both the lateral and longitudinal directions. As will be further explained below, the web structure 10a may be subsequently trimmed, folded, sealed, welded and/or otherwise manipulated to form a disposable garment 10 in final form and for packaging. In this regard, the composite web structure 10a is referred to as being finishable to form a disposable absorbent garment. In particular, the view of FIG. 2 is provided to reveal with clarity most of the major elements of the disposable absorbent garment 10 and/or web structure 10a according to the present invention.

It should first be noted that, upon review of the detailed description and the drawings provided herein, it will become apparent to one of ordinary skill in the art that the present invention is also applicable to other disposable absorbent articles and, more particularly, to disposable absorbent garments other than training pants and adult incontinence garments. The present invention is not intended to be limited to the structures and processes specifically described and illustrated herein.

Referring to FIG. 2, the garment 10 features a layered assembly or composite web structure 10a that includes a liquid-permeable inner layer or topsheet 16, a backsheet assembly including a hydrophobic and liquid permeable nonwoven backsheet 18 and a liquid-impermeable poly film barrier 60 and an absorbent core 36 disposed therebetween. The web structure 10a may be described further with reference to a longitudinally extending central axis A and a laterally or transversely extending central axis B. Along the longitudinal axis A, the garment 10 features a front waist region 20 having a front edge or front longitudinal end 52, a back waist region 22 having a back edge or back longitudinal end 54, and a crotch region 24 extending between the front waist region 20 and the back waist region 22. Along the lateral direction, the garment features left ear region 26a, central body region 28, and a right ear region 26b. Similarly, the back waist region 22 includes a left ear region 26a, a central body region 28, and a right ear region 26b. An elasticized leg cuff 38 extend between the front waist region 20 and the back waist region 22 on either side of the absorbent core 36. Described further below, the leg cuffs 38 or at least a portion of the leg cuffs 38 are formed between the ear regions 26a, 26b and the waist regions 20, 22.

The web structure 10a also has a longitudinal side edge 88 that extends between each pair of ear regions 26a, 26b and is spaced on each side of the absorbent core 36. As shown in FIG. 2, the side edges 88 are not straight lines but includes curves which help form the generally hourglass shape of the composite web structure 10a. Further, each of the ear regions 26 has a side edge area 30. During a later stage in the manufacturing process, the pair of ear regions 26a are joined together by mating their respective side edges 30 so as to form a side seam 34 (see FIG. 1) and a leg opening 14. The ear regions 26b are similarly joined to form a second side seam 34 and a second leg opening 14, and also to form a waist opening 12. It should be understood that the pair of ear regions 26a or 26b may be joined together by employing procedures well known to those skilled in the art (e.g., by ultrasonic welding, thermal bonding, or use of an adhesive).

When the garment 10 is properly worn about the waist region of the user, the topsheet 16 (and leg cuffs 38) generally contacts the buttocks of the user while the backsheet 18 faces outwardly from the body of the user. Further, the front waist region 20 of the garment 10 is situated at the front waist area of the user and the back waist region 22 is situated at the back waist area of the user, while the crotch region 24 is situated between the legs of the user and at the crotch area. As for the ear regions 26, each pair of adjoined ear regions 26a, 26b is designed to fit snugly about the side waist region of the user with the side seams 34 positioned preferably in a substantially vertical orientation.

As used herein for the purpose of description, each of the term "backsheet", "backsheet assembly", or "outer layer of the garment" refers to any sheet, layer or composite that covers at least the core 36, but preferably extends laterally beyond the core 36 toward the side edges 30 and longitudinal side edges 88 of the garment 10 or web structure 10*a*. Further, the term "backsheet", "backsheet assembly" or "outer layer of the garment" may refer to any assembly, unitary or integrally, of sheets, layers, or composites applied at least over the core 36, and any part, portion, region or section thereof. For example, the backsheet may have applied thereon a film material and/or graphics. The backsheet and film material may be referred to as one structure or as individual structures or layers.

Figure 3:
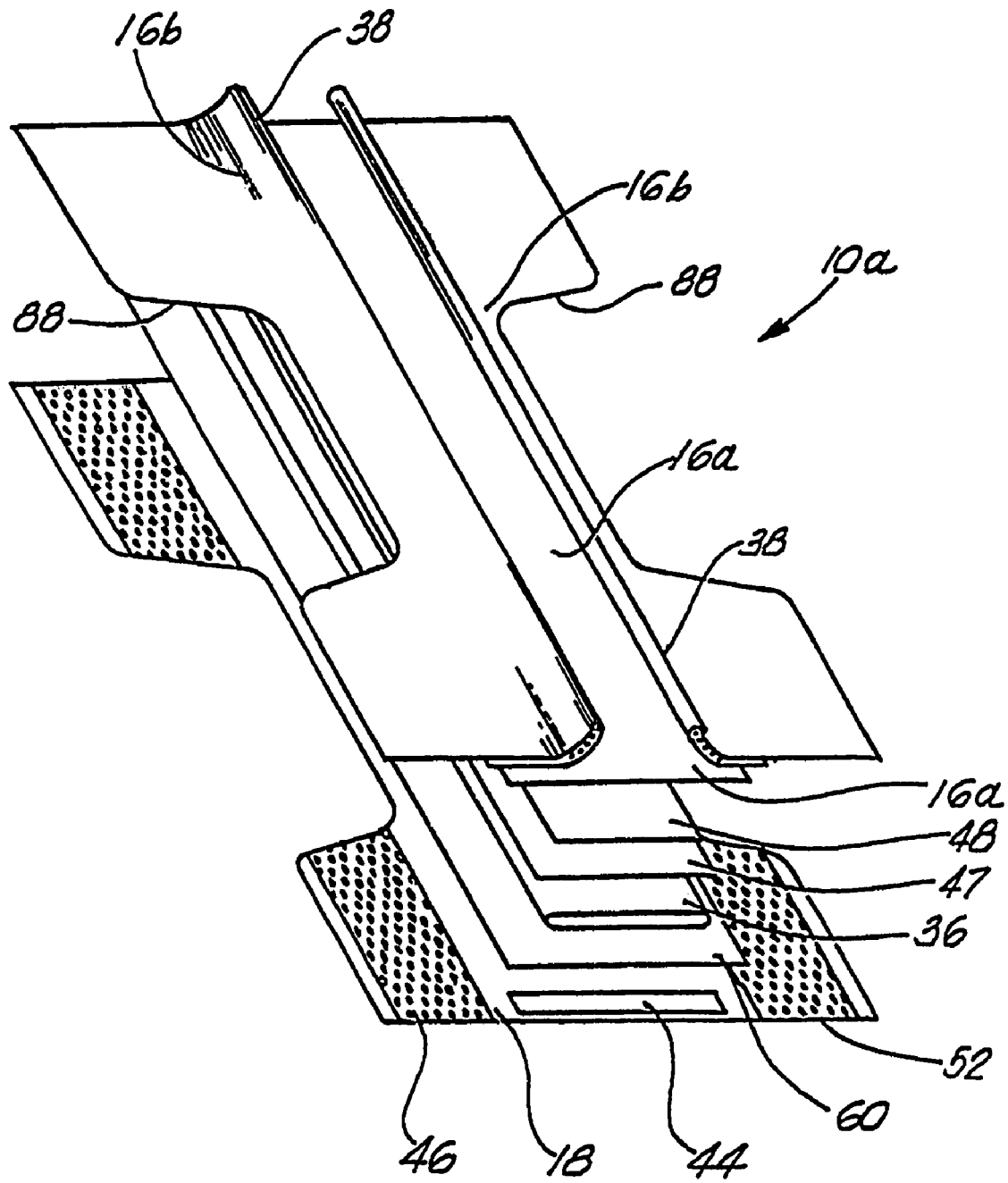
FIG. 3 is an exploded view of the disposable garment of FIG. 2.

The backsheet 18 may be constructed from a number of different suitable materials and, preferably, may have a breathable or vapor-permeable attribute (distinguishing it from liquid-permeable) so that air can pass therethrough. In the embodiment of FIGS. 1–8, the garment 10 (or web structure 10*a*) is equipped with a "backsheet-poly assembly" comprising a backsheet material 18 of a hydrophobic, vapor-permeable, nonwoven material and a polyolefin film mask or film barrier 60 that is laminated or otherwise applied onto the backsheet material 18 (see FIG. 3). In various embodiments, the film barrier 60 may or may not be vapor-permeable. Preferably, the film barrier 60 may be applied as a mask or sheet in a central area of the web structure 10*a*, as shown in FIG. 3. The film barrier 60 has an overall width that is less than the width of the other backsheet materials but sufficiently wide to cover the absorbent core 36.

One suitable construction for the backsheet assembly 18 includes an outer layer of spunbond polypropylene fiber with a basis weight of about 15 gsm (available from BBA Nonwovens, of Simpsonville, S.C.) and a polyethylene film of about 0.5 mil (0.0005") thickness adhesively laminated to the outer layer. Such a polyethylene film is available from, and manufactured by, Exxon Chemical USA, of Houston, Tex. The film may be laminated using adhesive available from National Starch & Chemical Company of Bridgewater, N.J. Yet another suitable construction for the backsheet 18 includes a web of spunbond or SMS (spunbond\meltblown\spunbond) nonwoven material and breathable or non-breathable films of 0.5 mils to 2.0 mils in thickness.

As shown in FIG. 3, the backsheet 18 is a sheet that provides the outer layer of each of the ear regions 26 as well as the outer layer of the rest of the front and back regions 20, 22 and the crotch region 24. Thus, the outer layer of each ear region 26 may be referred to as being unitary with, and forming a lateral extension of, the rest of the backsheet material. The backsheet 18 therefore extends up to and forms, at least partially, a side edge of the ear regions 26 and the web structure 10*a*.

In an alternative embodiment, the backsheet 26 may include a central section and a pair of left and right side panels or sheets which are distinct from the central section. Each of the side panels is joined to and, thereby, integrated with the central section. The left side panel extends between each of the left ear regions 26*a* and provides an outer layer common to both ear regions 26*a*. Similarly, the right side panel extends between each of the right ear regions 26*b* and provides an outer layer common to both right ear regions 26*b*. In yet another embodiment, the backsheet 18 includes, in addition to a central section, four separate side panels: a front right ear panel, a back right ear panel, a front left panel, and a back left panel. Each of the panels forms an outer layer of an ear region 26 and is joined to, and integrated with, the central section of the backsheet 18.

The absorbent core 36 is generally elongated and rectangular in shape. As best shown in FIG. 2, the core 36 is generally centered about the longitudinal axis A and laterals axis B of the garment 10, and firmly secured between the topsheet 16 and backsheet 18. The core 36 is preferably made of an absorbent composition adapted to absorb bodily liquids received through the topsheet 16. Typically, the absorbent composition includes a fluffed wood pulp component for wicking and structural integrity and a high absorbency material (or super absorbent) for containing liquids. However, the garment 10, according to the present invention, is equally adapted to utilize absorbent cores of varying shapes and compositions, as well as other types of cores known in the art.

As used herein for purposes of description, the term "topsheet", "topsheet assembly" or "inner layer of the garment" may refer to any sheet, layer or composite that covers at least the core 36, but preferably extends beyond the core 36 toward the side edges 30 and longitudinal side edges 88 of the garment 10 or web structure 10*a*. Further, the term "topsheet", "topsheet assembly" or "inner layer of the garment" refers to any assembly, unitary or integrally, of sheets, layers, or composites applied at least over the core 36, and any part, portion, region or section thereof.

The topsheet 16 may be constructed from a wide range of suitable materials including nonwoven webs of natural fibers (e.g., wood or cotton) or synthetic fibers (e.g., polypropylene or polyester), a combination of such webs or fibers, or apertured film. One suitable topsheet material is a 15 gsm spunbond polypropylene from Avgol Nonwoven Fabrics of Holon, Israel. In addition, the topsheet 16 may be treated with a surfactant to facilitate liquid transfer, especially at a central zone of the topsheet 16 over the core 36, and an inner surface of the topsheet 16 may be treated with a chemical to increase the surface tension of liquid passing through the material.

Referring to the web structure 10*a* of FIG. 3 and also FIG. 4, the topsheet 16 may be formed from a three-piece structure including a center section 16*a* disposed above (but not necessarily directly above) the absorbent core 36 and two lateral side sections 16*b* each laterally extending from the center section 16*a*. The lateral end or edge sections 88 of the lateral side sections 16*b* form the lateral ends or edges 88 of the web structure 10*a* (and of the ear portions 26). Referring to FIG. 4, the proximal end or edge sections of lateral side sections 16*b* are turned upwardly and provide an inwardly folded edge 90. These proximal edge sections 90 form an outer layer or outer cuff section 38*b* of leg cuff 38 that is joined with a substantially hydrophobic and impervious inside (or inner) layer or inside cuff section 38*a* of the leg cuff 38.

The inside cuff section 38*a* is preferably formed from a substantially hydrophobic and impervious material substantially similar to or the same as the polymeric material from which the film barrier 60 is made. Referring to the cross sectional view of FIG. 4, the inside cuff section 38*a* extends downwardly from the folded edge so as to engage an outer edge of center section 16*a* (near the top of the core 36) and, then, further downwardly to engage the film barrier 60 (near or below the bottom of the core 36). The inside cuff section 38*a* of the leg cuffs 38 may engage each of the outer edge of the central section 16*a* of the topsheet 16 and the film barrier 60 by adhesive or welding means and other joining means. Since the film barrier 60 and the inside cuff section 38a can be formed from the same substantially hydrophobic and impervious material, these two components may be easily integrated as one piece or applied as one piece in the manufacturing process.

Further, because the inside cuff sections 38a are connected to, integrated with or otherwise sealingly engages the film barrier 60, a continuous and substantially hydrophobic and impervious "bathtub-like" containment structure or barrier is formed under and on both sides of the absorbent core 36. The bottom and side walls of this bathtub-like containment structure is provided by the film barrier 60 and the pair of inside cuff sections 38a respectively. Accordingly, the inventive garment 10 features a unique containment structure that significantly reduces the possibility of leakage from the core area of the garment 10. In particular, the engagement of the side wall or inside cuff section 38a with the bottom or film barrier 60 of the bathtub-like containment structure prevents migration of waste (from the area of the core 36) underneath the cuff 38 toward the sides of the garment 10.

The leg cuffs 38 are preferably positioned on either side of or spaced from longitudinal axis A and outboard of the core 36, and extends generally upwardly from the topsheet 16 (i.e., toward the user). The longitudinal ends of the cuffs 38 may be attached, for example, to the topsheet 16 in the front and rear waist regions 20, 22. Preferably, the ends of the leg cuffs 38 are tacked down inwardly and attached, for example, by adhesive, to the web structure 10a. Such a construction biases the cuff 38 inwardly and is generally considered to cause the cuff 38 to exhibit improved leakage prevention properties.

Preferably, the leg cuffs 38 are equipped with one or more elastic material layers or members 40, which extend along a substantial length of the leg cuffs 38. In a common application, the elastic members 40 are placed within or underneath the leg cuffs 38 while in a stretched condition and then glued to the cuff at least at their ends. When released or otherwise allowed to relax, the elastic members 40 retract inwardly. When the garment 10 is worn, the elastic members 40 function to contract the leg cuffs 38 about the buttocks of the user in a manner, which effects a seal between the garment 10, and the buttocks.

The leg cuffs 38 (or at least the outer cuff section 38b) may be formed by a number of alternative methods known in the art. One method involves gluing a separately constructed leg cuff or cuff section to the top surface of the web structure 10a. Another method requires forming the leg cuff or cuff section from the topsheet or the backsheet 18. Yet another method involves creating and folding noodle cuffs as disclosed in U.S. Pat. No. 5,536,350, which is hereby incorporated by reference.

In an alternative embodiment of the invention, a longitudinally stretchable leg gather is positioned proximately each longitudinal side edge 88. When the garment 10 is properly worn by the user, each leg gather encircles a leg of the user and effects a seal thereon to prevent leakage. Generally, the leg gather is formed with elastic members which are typically applied in the stretched or extended condition and are placed between the topsheet 16 and backsheet 18. The elastic members are glued or otherwise secured to one or both of the topsheet 16 or backsheet 18, or other material layer of the web structure 110a. Upon release from its stretched condition, the elastic members retract with the attached material layer and form gathered leg regions.

The present invention is adapted to use other leg gather constructions known in the art. Moreover, the present invention may utilize leg gathers in combination with leg cuffs 38 as described above or, alternatively, alone without leg cuffs.

As best shown in FIGS. 2 and 3, the web structure 10a and thus, the disposable absorbent garment 10, preferably includes, disposed between the central section 16a and core 36, an acquisition layer 48 and top tissue layer 47. The acquisition layer 48 (or surge layer) is preferably situated between the topsheet 16 and the core 36. One function provided by such an acquisition layer 48 is to spread out or dispense liquid flow received by the garment 10 so that liquid is distributed more evenly over the surface of the core 36. By slowing down the liquid flow, the core 36 has sufficient time to absorb the liquid received thereon. The acquisition layer 48 also serves to prevent the situation wherein the core 36 is saturated locally, while a substantial remainder of the core 36 is not absorbing liquid.

Therefore, FIG. 3 provides a cross-sectional view which depicts the various layers of the web structure 10a and the respective structural relationships of the layers. In further embodiments, the inventive garment 10 may utilize a multipurpose material as one of the layers. Such a multi-purpose material would then provide multiple functions, thereby eliminating the need for one or more of the above-described layers.

As best shown in FIGS. 2 and 3, the web structure 10a and thus, the disposable absorbent garment 10, is also equipped with an elastic waist band 44 that is inserted between the topsheet 16 and backsheet 18 and adjacent the central body regions 28 of each of the front waist region 20 and back waist region 22. In other forms of the invention, the waist band 44 may be omitted or may be extended substantially continuously along the top end of the front waist region 20 and back waist region 22, thereby encircling or partially encircling the waist of the user when the garment 10 is worn. The waistband 44 is preferably made of an open cell urethane foam materials available from General Foam, of Paramus, N.J.

Still referring to FIGS. 2 and 3, the web structure 10a of disposable absorbent garment 10 is further equipped with a stretchable material layer or member 46 (e.g., an elastic member) substantially incorporated with, and made a part of, one or more of the ear regions 26. As best shown in FIG. 3, the stretchable member 46 is preferably interposed between the topsheet 16 and backsheet 18 in the ear regions 26. The stretchable member 46 extends longitudinally from nearly adjacent a longitudinal end 52 towards the crotch portion 24 (i.e., about 5–6" long) and laterally from substantially proximate the central body portion 28 toward the side edge area 30. However, the stretchable member 46 should be spaced sufficiently inwardly from the side edge area 30 so as not to be affected by or to affect the attachment of the side edges 30 to one another to form the garment 10. Furthermore, the present invention is not limited to specifically sized or positioned stretchable members 46. Instead, the stretchable member 46 may assume a variety of shapes and sizes and may be positioned at various locations within the ear regions 26 as long as the stretchable member 46 provides the ear regions 26 with sufficient extensibility to accomplish joinder of the ear regions 26 to form a waist region.

When the ear regions 26 are joined by the welding/bonding process, there is formed an absorbent garment 10 having stretchable side waist regions formed by the pairs of ear regions 26a, 26b. The stretchable member 46 is designed and is positioned within the ear regions 26 to facilitate stretching of the ear regions 26 in the lateral direction. The garment 10, therefore, can extend around and contract toward the side waist region of the user, and effect a snug fit. In one alternative embodiment of the invention, a substantially continuous elongated stretchable member 46 is positioned along both the front waist region 22 and back waist region 20, thereby acting as a nearly continuous belt around the user. The continuity of the belt is interrupted only by the side seams 34. In such an embodiment of the invention, the foam waistband 44 is preferably eliminated.

In a unique aspect of the invention, the ear regions 26 are attached to the stretchable member 46 when the stretchable member 26 is in a stretched or extended configuration. In forming an ear region 26, the stretchable member 46 is first extended or otherwise stretched laterally and then the inside surface of the topsheet material and/or backsheet material at the ear region 26 is\are secured or otherwise attached to a corresponding surface of the stretchable member 46 by conventional adhesive or mechanical means. It is important to extend the sheet material(s) to an extent where it displays a smooth, flat outer surface, but not necessarily to the extent where the material stretches and/or deforms. When the stretchable number 46 is then allowed to contract or relax, the topsheet material and/or backsheet material contracts with it.

To illustrate, FIG. 4 depicts the ear region 26 having an outer layer provided by the single-sheet backsheet material and formed unitary with the rest of the backsheet 18, and an inner layer provided by the leg cuff lateral section 16b of the topsheet 16. The ear region 26 is shown immediately after a section of both the lateral section 16b and the backsheet 18 are attached to the stretchable member 46 (and also when the garment 10 is worn by the user). In this view, the stretchable member 46 is maintained in the stretched or extended configuration, and the top lateral section 16b and backsheet 18 each display flat, smooth outer surfaces 90, 92 respectively. FIG. 5 depicts the ear region 26 after the stretchable member 46 is released and allowed to contract laterally to a relaxed, contracted or unscratched configuration. Preferably, the stretchable member 46 contracts from an initial width of about 4½" to 5½" to a relaxed or contracted width of about 2" to 3". The layered composite or assembly that is formed by the leg cuff lateral sections 16b, backsheet 18 and stretchable member 46 is moved inwardly toward the leg cuff 38 and, as a result, the lateral width of the garment 10 is reduced (e.g., from about 15" to 16" across to about 11" to 12" across). Moreover, the outer surface 90 of the lateral section 16b and the outer surface 92 of the backsheet 18 are slacked and form wrinkles and undulations on both sides of the stretchable member 46 (i.e., exhibit gathers).

To further illustrate, the bottom plan view of FIG. 6 is provided to show the condition of the backsheet 18 when the stretchable member 46 (and the stretchable ear portion 26) is disposed in an extended or stretched configuration (e.g., when the garment 10 is worn by the user). In the extended configuration, the backsheet 18 displays a smooth, continuous outer surface 92. Thus, when the garment 10 is worn around the waist of the user, the front and back waist regions 20, 22 together display a continuous, smooth outer surface substantially all around the waist of the user except where it is interrupted by the side seams 34. Conversely, FIG. 7 is a bottom plan view showing the condition of the backsheet 18 when the stretchable member 46 is disposed in the contracted or unstretched condition (e.g., when the garment 10 is not being worn by the user). In this view, wrinkles and a series of undulations (i.e., exhibits gathers), characterize the outer surface 92 of the backsheet 18 at the ear region 26.

It should be further noted that neither the side section 16b nor the backsheet 18 is permanently elongated during the forming of the composite layer, or during normal subsequent wear. In other words, the topsheet 16 and backsheet 18 are not stretched beyond its elastic region, and in some processes are merely extended to smooth out the outer surface, but not stretched beyond that point. In summary, the topsheet 16 (i.e., top cuff 16b) and backsheet 18 are merely stretched or extended to form flat, smooth surfaces 90, 92 during manufacturing and when the garment 10 is worn about the user, but retracts to a wrinkled, contracted state when the garment 10 is otherwise not worn.

The stretchable member 46 may be formed from an elastic material, such as the material typically used for the elastic waistband 44, or any other material with the appropriate stretch and return properties. The stretchable member 46 may be also formed from a heat-activated elastomeric material or elastomer that is elasticized upon initial application of a pre-determined amount of heat. The heat-activated elastic also contracts from an extended configuration to a contracted condition upon the initial application of heat in the vicinity of the stretchable member 46. In a process which makes use of the heat-activated elastomer, sections of the topsheet 16 and backsheet 18 are fastened to opposite surfaces of a stretchable member 46 incorporating the heat-activated elastomer and then contract with the stretchable member 46 upon the initial application of heat to the elastic. The stretchable member 44 incorporating the heat-activated elastomer may stretch or extend laterally when the garment 10 is worn around the waist of the user and then retract to its contracted, relaxed or unscratched configuration when the garment 10 is not being worn. Further, the materials of the leg cuff lateral section 16b and the backsheet 18 can extend laterally with the stretchable member 46 to display flat, smooth outer surfaces 90, 92 at the ear regions 26 and then contract with the stretchable member to display outer surfaces 90, 92 characterized by wrinkles and a series of undulations, and exhibiting gathers.

Preferably, the stretchable member 46 is applied by first extending or stretching the stretchable member 46 laterally and then securing (or otherwise attaching) the inside surface of the topsheet material and/or backsheet material to the corresponding surface of the stretchable member 46 (which is in the stretched condition). This latter procedure may be implemented by a mechanical thermal bonding process such as ultrasonic or heat and pressure bonding practices, and, more preferably, by ultrasonic bonding process.

In any of the above bonding processes, the topsheet 16 is mechanically bonded to the backsheet 18 at localized bond sites or bond points 100, at which the topsheet 16 and backsheet 18 are joined together through the stretchable member 46 (see FIGS. 6 and 7). Preferably, an ultrasonic bonding process is employed to bond the topsheet 16 and the backsheet 18, through the stretchable member 46. Employment of this bonding process, creates holes or apertures at the bond sites 100 and through the stretchable member 46. These holes or apertures at the bond sites 100 provide breathability or air permeability to the ear regions 26a,26b (see also FIG. 6). More particularly, the holes at the bond sites 100 are created as a result of the selection of materials for the topsheet 16, backsheet 18 and stretchable member 46, and use of the ultrasonic bonding process. In this process, the non-woven materials (i.e., topsheet 16 and backsheet 18) requires substantially more energy to bond than the material selected for the elastic member 46 (i.e., a polymeric material). Accordingly, the level of ultrasonic bonding that is sufficient to bond the non-woven materials also causes the material for the elastic member 46 to fracture and/or disintegrate. As a result, the two non-woven layers bond together, but trap the polymeric material of the elastic member 46 therewith. Further, the hole that is blown or created through the elastic member 46 is larger than the bond site, and the two non-woven layers bond with each other through the center of the hole.

Furthermore, the inventive garment and manufacturing process provide a pattern for placement of the bond sites 100 on the ear region 26a,26b. The preferred pattern is a staggered pattern as shown in FIG. 6 which maximizes the spacing between bond sites 100 for a given number of bond sites 100. Importantly, the spacing between consecutive bond sites along direction of stretching (i.e., lateral direction) is maximized such that the elasticity of the ear region in this direction is not significantly altered nor compromised. A breathable ear region or side panel is, therefore, provided having adequate elastic properties and contracting force.

Although, the bond sites or holes may be formed in any shape, it is preferred to select a shape that is particularly adapted to staggering, such as the rectangular shape shown in FIG. 6. Such a shape, wherein the longitudinal dimension is significantly greater than the lateral dimension, provides a larger capacity for stretching in the lateral direction while minimizing the potential for propagating tears.

It is understood that it will be apparent to one skilled in the art, upon reading the detailed descriptions provided herein and viewing the accompanying Figures, to employ various conventional manufacturing elements (e.g., rollers, conveyors, etc.) and arrangements thereof to produce the garment and more particularly, a breathable, stretchable section of the garment as described above. Such manufacturing elements include those described and illustrated in pending application Ser. No. 09/215,473, entitled "Disposable Absorbent Garment Having Stretchable Side Regions." This application and invention are also assigned to the assignee of the present invention (hereby incorporated by reference).

The above-described inventive garment is particularly adapted for a method of manufacturing in which a web structure is advanced in the "in-line" or "machine" direction. The terms "in-line direction", "in process direction", and "machine direction" are used herein to refer to an orientation and travel of the composite web structure during the manufacturing process. When oriented in the "inline", "in process" or "machine" direction, the front or back waist regions is positioned ahead of the crotch region in the direction of conveyor travel with the other waist regions directly trailing the crotch region. This is different from the cross-machine orientation wherein the web structure is turned 90 degrees from the in-line or machine direction such that the crotch region and the waist regions are aligned along a lateral line that is normal to the direction of conveyor travel.

The manufacturing method may be regarded as beginning with the delivery of a continuous web structure comprising of an absorbent core, top tissue and acquisition layer (e.g., core assembly). Typically, the absorbent core is received from a drum former, delivered to a transfer roll and then onto a surface of a main conveyer. Each absorbent core is positioned on the conveyor such that its length is generally parallel to the machine direction.

The method further includes the use of a supply roll to continuously apply or otherwise provide the top tissue layer onto each absorbent core. Downstream of the supply roll, another supply roll and a cut and slip unit are situated. These units are conventional types which are readily available to one skilled in the art. The supply roll delivers the acquisition layer material to the cut and unit to form individual patches of the material which are spaced apart and then applied on top of the top tissue. This step therefor provides an acquisition layer on the composite web structure. A continuous web structure is thereby formed comprising absorbent core, top tissue and acquisition layer and is oriented in the in-line direction.

Next, this continuous web is moved toward the pad knife or cutting roll which is used to cut the composite web structure laterally between the absorbent core. Accordingly, this cutting step provides a plurality of individual, in-line composite web structures comprising absorbent core covered with top tissue and acquisition layer. A supply roll positioned downstream of the pad knife such that, as each web structure is conveyed thereto, a polymeric layer is applied or provided onto the bottom of the absorbent core. Application of the polymeric layer forms the film barrier layer beneath the absorbent core.

Upon or simultaneous with the step of applying the film barrier layer is the step of applying a three-piece topsheet assembly equipped with poly-on, elasticized leg cuffs onto the web structure. A composite structure including this topsheet assembly maybe constructed in a separate process or subprocess before it is delivered to the main conveyer and applied to the top of the composite web structure.

When the composite web structure including the three-piece topsheet having poly-lined leg cuff is attached to the web structure, the polyliner is joined with or otherwise engages opposite side edges of the barrier film. This engagement between the two substantially hydrophobic and impervious layers results in the bathtub-like containment structure disposed at least adjacent the bottom and sides of the core.

In what may be regarded as the next stage of the process, a web structure including backsheet and stretchable members is then applied to the composite web structure. This web structure may be constructed from a subprocess employing a subsystem which is separate from but converges onto the main conveyor. At the conveyor, the web structure is applied to the bottom of the composite web structure so as to form a lamination therewith.

A stretched ear region or side panel is, therefore, created that is made up of an elastomeric film laminated between the full width backsheet and the full width topsheet. In this respect, an elastic side panel or ear region becomes an integral part of the complete absorbent garment. Adhesive may be applied on the backsheet material and/or the stretchable member prior to these two elements coming into pressurized contact.

In a subsequent step in the process, the web structure is conveyed to a thermal-bonding module (e.g. employing ultrasonic or heat and pressure bonding practices). At the module, the composite webs 50, 49 are bonded together and through the stretchable member to form a side waist region. As described previously, energy from the preferred bonding process creates a hole in the stretchable member and allows for the topsheet material and the backsheet material to bond therethrough. This also creates a vent at the bond site through which air may pass.

After the bonding process, the resulting composite web may be held under vacuum and passed through a die cut station wherein the leg openings are cut out from each of the lateral sections and the corresponding section of the backsheet. Then, the continuous composite web structure is cut at a knife station to form individual web structures. Each web structure is subsequently folded and then passed through a seam welding station where side edge areas of the ear regions are joined together by any suitable method of bonding, including ultrasonic, thermal or adhesive bonding.

The folded and seamed composite web structure which, at this point, constitutes an individual absorbent garment is passed through a side panel tuck station where the side panel of the garment is folded between the front and back side panels before being delivered to a stacker.

For clarity, some subprocesses such as the application of waist elastic members and leg gathers to the web structure 10a are described. It should be understood, however, that the present invention is adapted to incorporating various constructions of these components and suitable methods of applying such constructions onto a composite web structure.

It should be noted that the web structure 10a and the components that make up the web structure are positioned in the in-line or machine direction C during the preferred manufacturing process (i.e., wherein the longitudinal axis A is coincidental with the direction of web travel). Applicant believes that positioning the web structure 10a in this manner furthers efficiency in the manufacturing process and promotes quality in the final product. In one aspect of the invention, the design of the web structure 10a and the garment 10, particularly the use of the stretchable member 46 instead of elongated elastics threads which are directed laterally across the width of the garment 10, allows for such an in-line process of manufacturing to be employed.

Although several embodiments of the present invention have been shown or described, alternate embodiments will be apparent to those skilled in the art and are within the scope of the present invention. Therefore, the invention is to be limited only by the claims.

What is claimed is:

1. A method of forming a breathable, stretchable section of a disposable absorbent garment, said method comprising the steps of:
    selecting a first material for a first material layer and a second material for a second material layer, whereby said first and second material layers are bondable by an ultrasonic bonding process;
    selecting an elastic material for a stretchable material layer;
    positioning the stretchable material layer between the first and second material layers to form a layer assembly;
    targeting one or more bond sites on the layer assembly for bonding one or more of the metered layers together; and
    securing the first, second, and stretchable layers together by ultrasonically bonding the first material layer with the second material layer at the one or more sites, whereby an aperture is formed through the stretchable material and whereby the first material layer and the second material layer substantially, completely bond through the aperture at the one or more bond sites, and such that the aperture provides a breathable passage therethrough.

2. The method of claim 1, wherein the step of selecting the first and second material includes selecting a topsheet material and a backsheet material layer, respectively.

3. The method of claim 1, wherein the step of selecting the first and second material includes selecting a first non-woven material and a second non-woven material, respectively.

4. The method of claim 1, further comprising the step of stretching the stretchable material layer to an extended configuration and performing the securing step when the stretchable material layer is in the extended configuration such that the first and second material layers are subsequently contractible and then extendible with the stretchable material layer.

5. The method of claim 1, wherein the targeting step includes longitudinally and laterally spacing the bond sites so as to create a staggered pattern of breathable bond sites on the stretchable section of the garment.

6. The method of claim 1, wherein the steps of selecting the first and second materials and the positioning step includes positioning the first, second, and stretchable material layers so as to form a stretchable side waist region of the garment after the securing step.

7. The method of claim 1, wherein the securing step defines a breathable, stretchable layer assembly having vent sites provided at the bond sites.

8. The method of claim 7, wherein the securing step defines, at each bond site, a hole through the stretchable material, a hole through the first material layer, and a hole through the second material layer, whereby the hole through the stretchable material layer is larger than the holes through the inner and outer material layers.

9. The method of claim 7, wherein the securing step forms an aperture being defined by a hole periphery of fragmented stretchable material.

10. The method of claim 7, wherein the securing step includes fragmenting the stretchable material to bond the periphery of the aperture therewith.

11. A method of forming a disposable absorbent garment having a breathable, stretchable side waist region, said method comprising the steps of:
    selecting a first material for a first material layer and a second material for a second material layer, whereby said first and second material layers are bondable by an ultrasonic bonding process;
    selecting an elastic material for a stretchable material layer;
    positioning the stretchable material layer between the first and second material layers to form a layer assembly;
    targeting one or more bond sites on the layer assembly for bonding one or more of the material layers together; and
    securing the first, second, and stretchable layers together by ultrasonically bonding the first material layer with the second material layer at the one or more sites, thereby forming a breathable, stretchable side waist region, whereby an aperture is formed through the stretchable material and whereby the first material layer and the second material layer substantially, completely bonds through the aperture at the one or more bond sites, and such that the aperture provides a breathable passage therethrough and a vent site for the stretchable side waist region.

12. The method of claim 11, wherein the step of selecting the first and second material includes selecting a topsheet material and a backsheet material layer, respectively.

13. The method of claim 11, wherein the step of selecting the first and second material includes selecting a first non-woven material and a second non-woven material, respectively.

14. The method of claim 11, further comprising the step of stretching the stretchable material layer to an extended configuration and performing the securing step when the stretchable material layer is in the extended configuration such that the first and second material layers are subsequently contractible and then extendible with the stretchable material layer.

15. The method of claim 11, wherein the targeting step includes longitudinally and laterally spacing the bond sites so as to create a staggered pattern of breathable bond sites on the stretchable section of the garment.

16. The method of claim 11, wherein the securing step defines a breathable, stretchable layer assembly having vent sites provided at the bond sites.

17. The method of claim 16, wherein the securing step defines, at each bond site, a hole through the stretchable material, a hole through the first material layer, and a hole through the second material layer, whereby the hole through the stretchable material layer is larger than the holes through the inner and outer material layers.

18. The method of claim 17, wherein said securing step includes fragmenting the stretchable material to bond the periphery of the aperture therewith.

19. A method of forming a disposable absorbent garment having a breathable, stretchable side waist region, said method comprising the steps of:

selecting a first material for a first material layer and a second material for a second material layer, whereby said first and second material layers are bondable by an ultrasonic bonding process;

selecting an elastic material for a stretchable material layer;

positioning the stretchable material layer between the first and second material layers to form a layer assembly;

targeting one or more bond sites on the layer assembly for bonding one or more of the material layers together; and securing the first, second, and stretchable layers together by ultrasonically bonding the first material layer with the second material layer at the one or more sites, whereby an aperture is formed through the stretchable material and whereby the first material layer and the second material bond through the aperture in a substantially complete manner and such that the aperture provides a breathable passage therethrough, and whereby the first material layer bonds with the second material to form the aperture by fragmenting the stretchable material to bond the periphery of the aperture therewith.

\* \* \* \* \*